United States Patent [19]

Webb et al.

[11] Patent Number: 4,769,829
[45] Date of Patent: Sep. 6, 1988

[54] CT SCANNER AND DETECTOR THEREFOR

[75] Inventors: Steve Webb, Teddington; Martin O. Leach, Surrey; Peter Newbury, Kent, all of England

[73] Assignee: The Institute of Cancer Research, Gardens, United Kingdom

[21] Appl. No.: 826,944

[22] Filed: Feb. 7, 1986

[30] Foreign Application Priority Data

Feb. 7, 1985 [GB] United Kingdom ............... 8503121

[51] Int. Cl.⁴ .............................................. G21K 1/12
[52] U.S. Cl. .................... 378/19; 378/146; 378/147
[58] Field of Search ................ 378/19, 146, 147, 150

[56] References Cited

U.S. PATENT DOCUMENTS

| 3,894,234 | 7/1975 | Mauch et al. | 378/146 |
| 3,934,142 | 1/1976 | Hounsfield | 378/19 |
| 4,075,491 | 2/1978 | Boyd | 378/19 |
| 4,205,375 | 5/1980 | Inouye et al. | 378/901 |
| 4,241,404 | 12/1980 | Lux | 378/19 |
| 4,242,583 | 12/1980 | Annis et al. | 378/146 |
| 4,260,898 | 4/1981 | Annis | 378/146 |
| 4,324,978 | 4/1982 | Kalender et al. | 378/150 |
| 4,541,107 | 9/1985 | Rossi | 378/146 |

FOREIGN PATENT DOCUMENTS

| 0881464 | 11/1961 | United Kingdom | 378/146 |
| 1391042 | 6/1972 | United Kingdom | |
| 1283915 | 8/1972 | United Kingdom | |
| 1381202 | 1/1975 | United Kingdom | |
| 1513601 | 3/1975 | United Kingdom | |
| 1468810 | 3/1977 | United Kingdom | |
| 1546158 | 5/1979 | United Kingdom | |
| 2076250 | 11/1981 | United Kingdom | 378/146 |
| 2084829 | 4/1982 | United Kingdom | 378/146 |
| 2089033 | 6/1982 | United Kingdom | |
| 2144960 | 3/1985 | United Kingdom | |

Primary Examiner—Janice A. Howell
Assistant Examiner—David P. Porta
Attorney, Agent, or Firm—Antonelli, Terry & Wands

[57] ABSTRACT

A CT scanner comprises a rotatable gantry 1 carrying an X-ray source 3 which provides a fan-shaped beam of X-rays and an X-ray detector 10 which scans the X-ray intensity along a line in the plain of the beam. The gantry is rotatable about an axis A relative to a couch 2 which supports the patient under investigation. The X-ray detector 10 comprises two concentric X-ray masks exposed around a scintillator tube; the two masks having helical X-ray transmissive apertures, the helices being of opposed orientation so that rotation of the masks in opposite directions causes the exposed area of the scintillator tube to move along its length.

10 Claims, 7 Drawing Sheets

CT SCANNER AND DETECTOR THEREFOR

The present invention relates to a CT (computerised tomography) scanner and detector therefor.

Information derived from patient cross-sectional images produced by computerised tomography is of value in planning radiotherapy treatment, as it can provide the location of major tissue interfaces, as well as the body outline and tissue electron density.

High resolution CT scanners can provide diagnostic information about the extent of the tumour and the degree of invasion of surrounding tissues, but diagnostic information is not required when planning dosimetry where radiation is delivered to an organ or the whole body, rather than to a well localised lesion within an organ. A slower rate of data collection is also acceptable. This is particularly the case with breast cancer, total body irradiation and rhabdomyosarcoma.

In breast cancer, successful local control produces an increased survival rate (Suit et al, 1982) and the achievement of a uniform dose to the treated tissue, without high dose areas or 'hot-spots' in normal tissues such as the lung, ribs and muscle, is fundamental to achieving the good cosmetic result required in conservative management.

According to the present invention we provide a CT scanner comprising an X-ray source arranged to provide a fan-shaped beam of X-rays and an X-ray detector arranged to produce an electrical output representative of a scan of the X-ray intensity across the fan. Conveniently, the detector is a photon-counting detector and is arranged to scan in the plane of the fan, along a line perpendicular to the central axis of the fan; preferably the line is straight, although it may be curved. The source and detector are preferably mounted on a rotatable gantry so as to be rotatable around a patient so that the exposure/scanning is conducted as the gantry is rotated; this can speed up the acquisition of data but at the expense of rather more complex computation being required during processing of the data, to account for the combined motion resulting from the scanning movement of the scanning aperture and the rotation of the gantry.

The invention also relates to a novel form of X-ray detector which may be used in the CT scanner according to the invention and in other applications and provides an X-ray detector incorporating a scintillator/detector arrangement adapted to produce at an output a scan of X-ray intensity along a line. Suitably, the scintillator comprises a scintillator tube and an arrangement is provided for selectively exposing the material of the tube to X-rays at a point which moves, during the X-ray scan, along the length of the tube. This means may comprise an X-ray mask having an X-ray-transmissive aperture which by a suitable drive arrangement progresses along the length of the tube during a scan. The aperture may be formed by the intersection of a helical, X-ray transmissive cut-out or scroll on a mask surrounding the tube and another such scroll of opposite sense and/or a linear aperture along the length of the tube. The use of two, oppositely sensed, scrolls is preferred to just a single scroll and a linear aperture as a linear aperture by itself would represent a line along the length of the scintillator which has less shielding than the remainder. In a preferred embodiment, there are three apertures, one in a linear collimator and two provided by concentric collimator tubes having helical scrolls of opposite senses on them, these being driven for rotation so as to produce an aperture which scans along the length of the tube.

BRIEF DESCRIPTION OF THE DRAWINGS

The invention will be further described by way of example with reference to the accompanying drawings in which.

In the following, the invention will be described with reference to its application to a radiotherapy dosimetry scanner to provide the necessary CT information by attaching a high count-rate position-sensitive detector to a modifed radiotherapy simulator. This approach differs from two earlier methods, using X-ray film and a modified isotope scanner. The use of a photon counting detector is fundamentally different from the analogue camera-screen combination intended to produce a more linear and controllable system. Digital data collection, processing and reconstruction methods are used at all stages in use of the illustrated embodiment of the invention from counting the detected photons to displaying the final reconstructed image.

The scanner provides the facilities necessary for planning and simulating the radiotherapy of breast cancer, and may be provided with an image intensifier for more general simulation purposes when CT information is not used.

Figure 2:
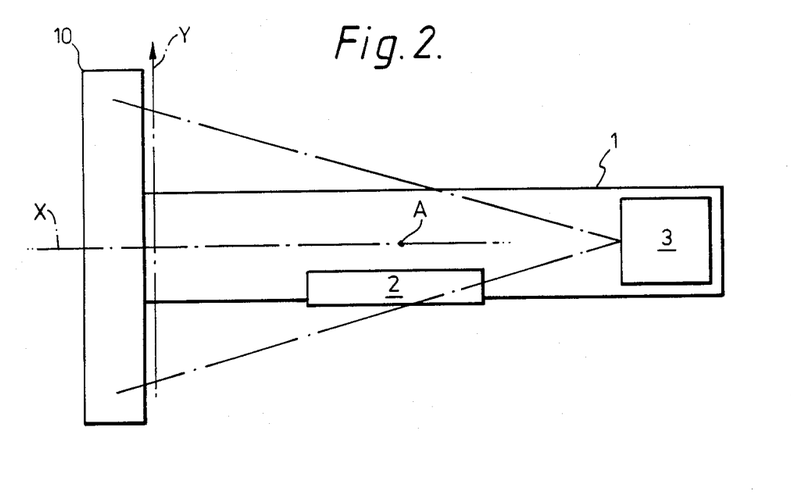
FIG. 2 is a view showing a CT scanner embodying the present invention and incorporating the detector of FIG. 1.

Referring to FIG. 2, this is a somewhat schematic end view intended to show the general arrangement of the illustrated CT scanner embodying the present invention. A gantry 1 is mounted for rotation about an axis A by means not shown relative to a couch 2 on which the patient lies. On one of its two limbs, the gantry carries an X-ray source 3 which provides a fan shaped beam of X-rays, while on the other limb, which is the opposite side of the axis A to the first limb, is a detector 10 embodying the present invention. Broadly, as the gantry 1 slowly rotates, the detector 10 is operated to detect the intensity of X-rays received along a line Y perpendicular to the axis X of the X-ray source 3. The results of a series of projections used to build up a cross-sectional image and, by moving the couch 2 perpendicular to the plain of FIG. 2 and repeating the procedure, a number of cross sections can be built up.

Figure 1A:
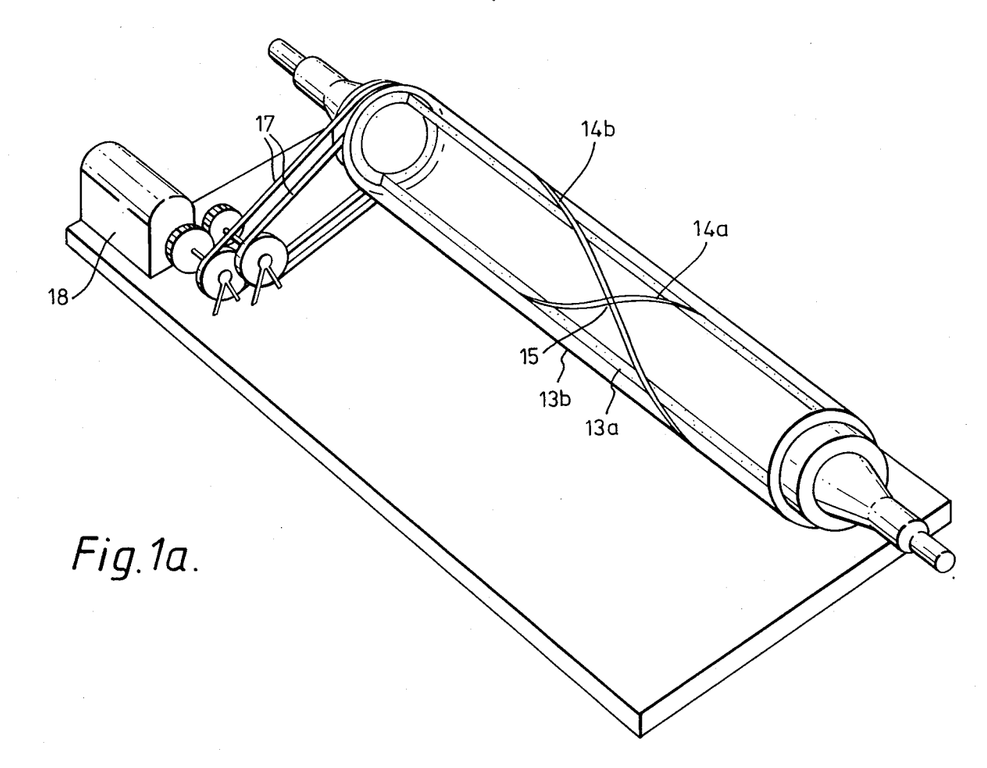
FIG. 1(a) is a perspective view of a detector according to the present invention.
Figure 1B:
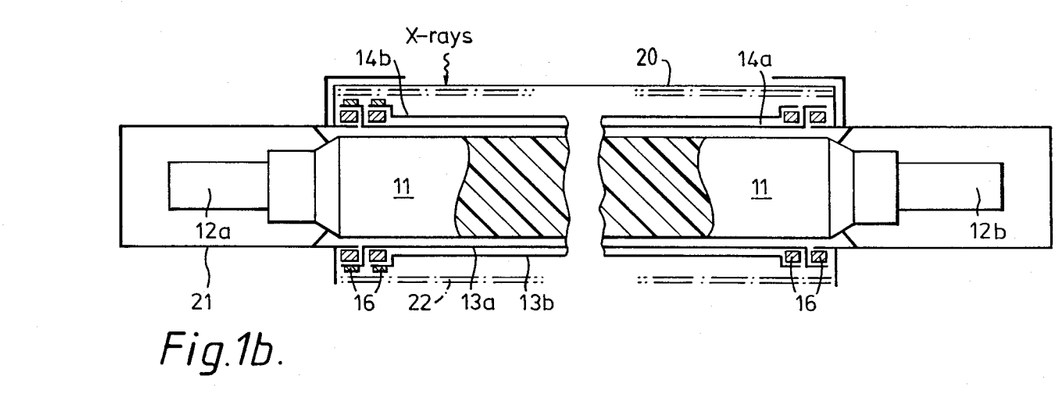
FIG. 1(b) is a longitudinal sectional view of FIG. 1(a)
Figure 1C:
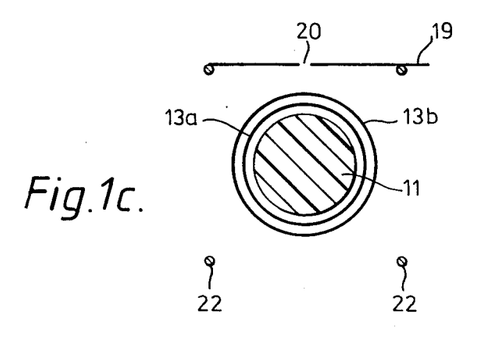
FIG. 1(c) is a cross-sectional view of the detector.

The detector 10 for this scanner is shown schematically, with the upper collimator omitted for clarity, in FIG. 1b, and in cross-section in FIG. 1c. The detector comprises a rod of plastic scintillator 11 (NE102A, Nuclear Enterprises, Sighthill, Edinburgh) of total length 92 cm, and 10 cm in diameter, with the final 5 cm tapered at each end to mate with two EMI 9821B fast linear focussed photomultiplier tubes 12a & 12b. This rod of scintillator is surrounded by two concentric lead collimators 13a & 13b, each with a 3 mm wide scroll 14a, 14b (a single helix) cut through the lead to the aluminum support. The scrolls are of opposite sense and so arranged that they intersect to produce a diamond shaped collimated lead-free aperture. These two collimators are supported on bearings 16 and driven in opposite directions by belt drives 17 from a gearbox and synchronous motor 18. The effect of this method of driving the collimators is for the lead-free aperture to repeatedly traverse the length of the detector in one direction. As the distance travelled by the aperture 15 is directly related to the number of pulses delivered to the motor, the output of the photomultiplier tubes 12a, 12b can be directly related to the position of the aperture 15, giving the detector its position sensitivity.

The lead on each of the two concentric collimators is 2 mm thick, and additional collimation may be provided by a static sheet 19 of 3 mm thick lead (FIG. 1c), supported on an aluminium plate, with a 3 mm wide slot 20 cut through the lead and aluminium, along the length of the detector, so as to admit the fan beam from the X-ray source. The tubes and scintillator are mounted in a light tight enclosure 21. An optical sensor (suitably of the interruptor type) monitors the rotation of the collimator, to indicate when the scanning aperture is at the end of the detector and thus to mark the start of a projection. The sensitive length of the detector is 65.2 cm.

The outputs from the two photomultiplier tubes viewing the bar of plastic scintillator are summed by a summing amplifier 31, so that the summed signal does not vary markedly with displacement of a radiation source along the length of the detector.

Figure 3:
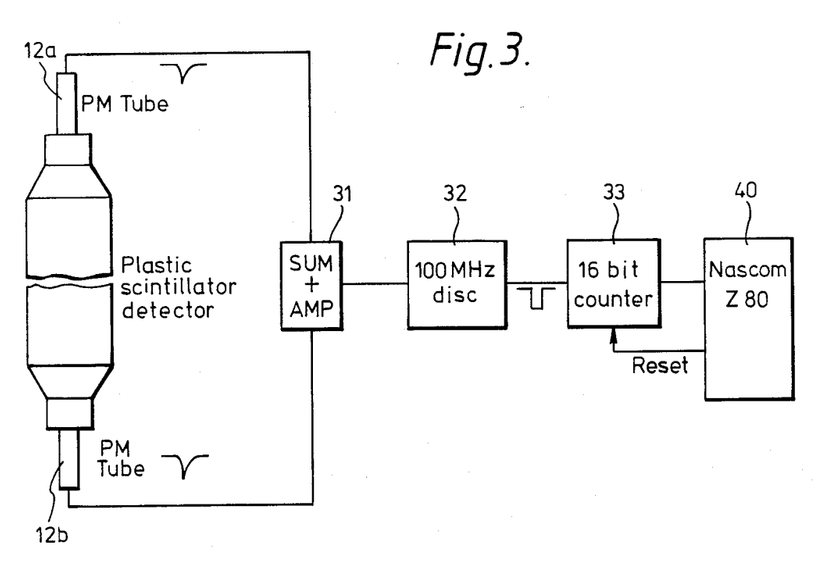
FIG. 3 is a block diagram showing how the signals from the detector of the scanner are processed.

The circuitry used with the detector are shown in FIG. 3. The photo-multiplier high-voltage supplies are provided by two NE 5353 power supplies each capable of providing a current of 5 mA. The dynode chains of the photomultipliers are preferably designed to provide a high-current fast rise-time pulse with a time constant of about 10 nanoseconds and this, coupled with the intrinsic rapid rise and decay of the light pulses from the plastic scintillator, produces a short pulse (about 14 nanoseconds). The summed output from the two photomultiplier tubes from the summer/amplifier 31 is fed into an EG and G T105/N fast leading-edge discriminator 32 which produces a 20 nanosecond wide output logic pulse and can process input pulses up to a frequency of 150 MHz. The discriminator effectively filters out pulses whose leading edges are of lower than a preselected amplitude; it could also be arranged to filter out pulses whose leading edges exceed a particular amplitude so as to provide a detection window into which a pulse has to fall in order to be counted.

The output logic pulse from the discriminator 32 is fed via an optical coupler to minimize noise propagation into a 16 bit 35 MHz counter 33 which is interfaced to a Nascom Z80 microprocessor 40.

As will be appreciated from the above, the counter 33 thus counts the number of photons, rather than integrates the energy of the photons as in conventional X-ray detectors.

Count rates of up to 3 MHz with no attenuating material are observed with the detector system when the PM tubes are supplied at 1.8. The microprocessor 40 monitors the mains frequency and ensures that the register is re-set only at integer multiplies of 100 Hz., the frequency being locked to the mains frequency when each projection is commenced.

Figure 4:
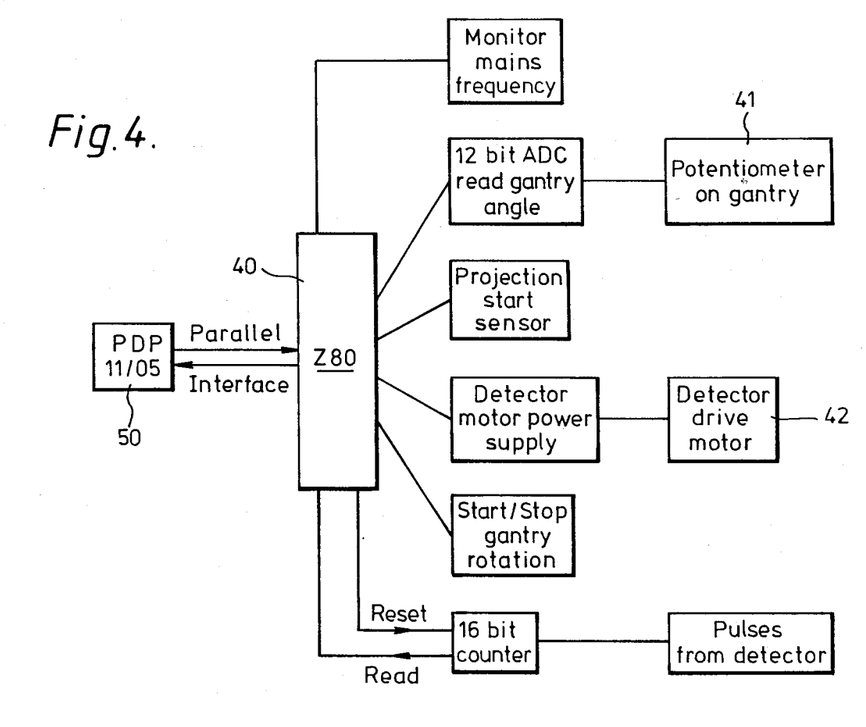
FIG. 4 is a block diagram showing the overall arrangement of the control circuitry of the scanner.

The controlling electronics for the simulator and detector is shown in FIG. 4. The scanner is controlled by a PDP11/05 computer 50 with dual 2.5 megabyte discs for projection data and software storage. This computer 50 performs data storage, controls the acquisition of experimental data and can perform image reconstruction. The PDP11/05 is interfaced to the NASCOM Z80 microprocessor 40 via a DR 11C parallel interface which permits rapid data transfer. The Z80 microprocessor is interfaced to the simulator gantry and to the detector and controls their movements (by activating motor 42 and the gantry drive motors) and projection data acquisition. The angular orientation of the simulator gantry is obtained by monitoring the voltage developed across a high-precision servo potentiometer 41 driven by the gantry rotation, via and ADC which is interrogated at the start of each projection.

Figure 5:
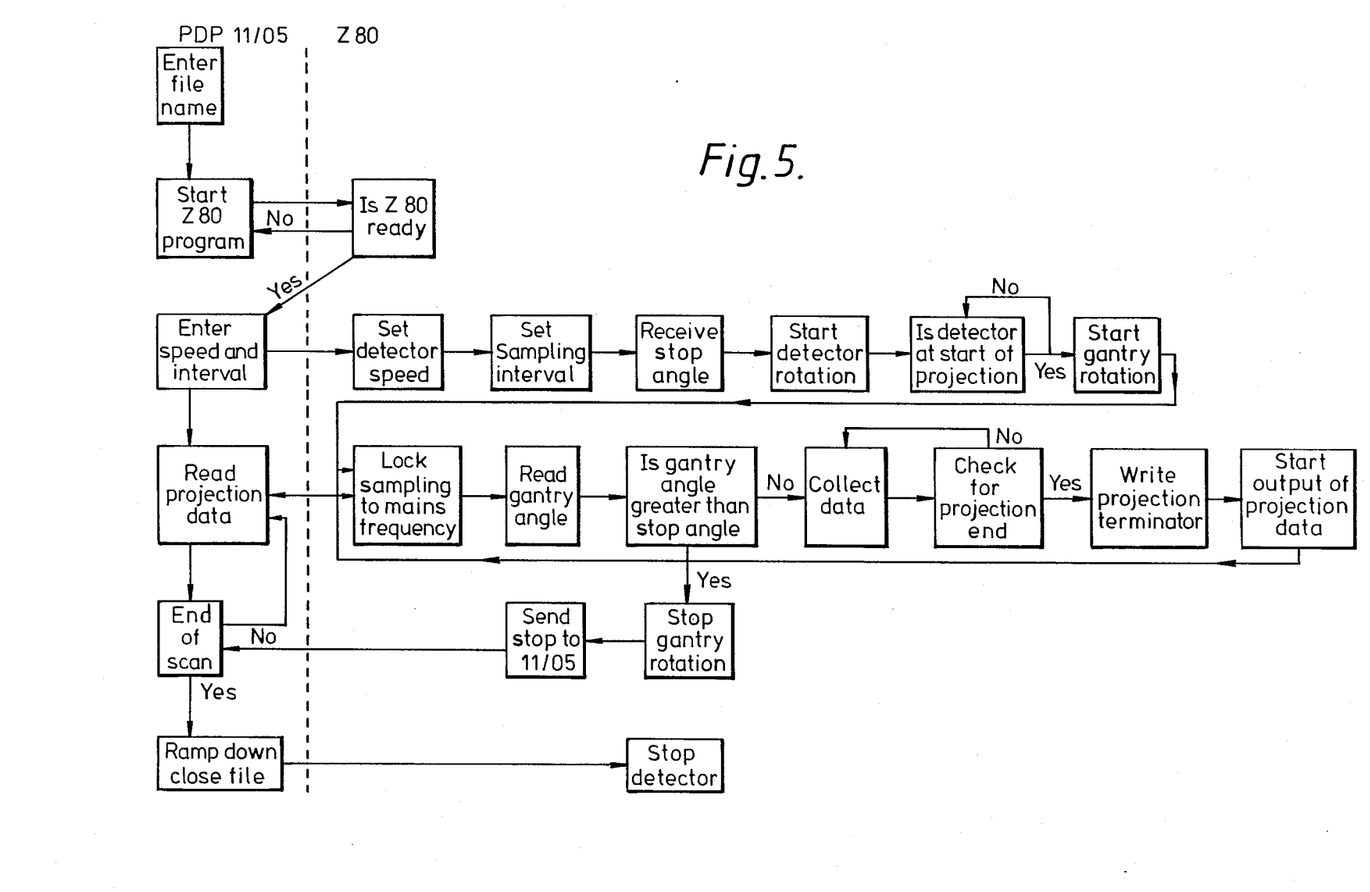
FIG. 5 is a diagram showing the manner in which the scanner is programmed to operate.

To commence scanning, the PDP11/05 issues an instruction to the Z80 and transfers information concerning the angle of the gantry relative to the vertical, the detector sampling interval and the collimator rotion speed to the Z80. A block diagram of the computer programs is shown in FIG. 5. The X-ray source 3 is switched on and the detector collimators are ramped up to their correct rotational speed. Once the detector collimators are rotating at the pre-set speed, the simulator gantry commences rotation. Projection sampling now commences. When the diamond shaped aperture of the collimator reaches the end of the detector, signalling the end of one and the beginning of the next projection, the gantry angle is measured by interrogating the ADC monitoring the gantry rotation angle. This value is stored in the Z80 memory. The step interval of the detector is then synchronized to the mains frequency supplying the X-ray set to ensure that only an integer number of full 100 Hz cycles are monitored in each detector sampling interval, a necessary step when using a single phase X-ray tube. The number of photons recorded by the register during each sampling interval is then stored in the Z80 memory. When the next end-of-projection signal is received, the stored data is output to the PDP11/05 via the parallel interface and simultaneously the next projection data are acquired. This continues until the measured angle exceeds the pre-set gantry stop angle. The gantry rotation and data collection are then terminated. The detector collimator rotation is ramped down and the data file on the PDP011/05 is closed.

The detector has usually been operated with either one or two 10 msec X-ray pulses per 2 mm projection sampling interval. Each projection therefore takes 3.31 or 6.62 seconds to acquire. The gantry rotation speed is independently set, and typically 90 projections are recorded in either 5 or 10 mins.

Following collection, the logged object data are subtracted from a logged blank reference air scan. This allows systematic changes in detector output with position along the gantry and with gantry angle to be corrected, and also ensures that the projection data represent line integrals of X-ray absorption through the object. The projection data can then be median window filtered (Leach et al, 1983) prior to reconstruction, to minimise projection noise while retaining edge information. The projection collection geometry presents an unusual problem in data reconstruction. Static projections at known equispaced angles are not collected, rather the detector is sequentially sampled along its length, while the continual rotation of the gantry produces a further displacement of each sampled point, thus a normal fan beam reconstruction algorithm cannot be used without modification. The particular geometrical problem posed by this scanner has been solved by Herman (Herman, 1982) who has shown that the problem can be reduced to a conventional fan-beam projection problem by the use of virtual source and detector positions. This reduction has been combined with a modified divergent beam convolution and back projection reconstruction algorithm (Webb, 1982) which permits the degree of roll-off of the frequency window to be varied. An additional modification to Herman's algorithm is necessary. The back projection algorithm has to be modified to correct for data being collected on a straight rather than curved detector array. The algorithm uses a fixed virtual source position, and each virtual projection is centered about the measured gantry angle appropriate to the centre of each measured projection. Reconstruction is normally performed on a VAX 11/750 computer, with a reconstructed of 90 projections into a 256×256 image array taking approximately 22 mins. Following reconstruction, the patient cross-sectional information may be displayed on a Sigma display or on a Siemens Evaluskop display, or transferred to an RTplan or Evados treatment planning system for viewing, hard copy and treatment planning. Alternatively, the image data can be used to generate body outline and tissue interface contours for planning systems such as RAD8 or for hand planning.

Figure 6A:
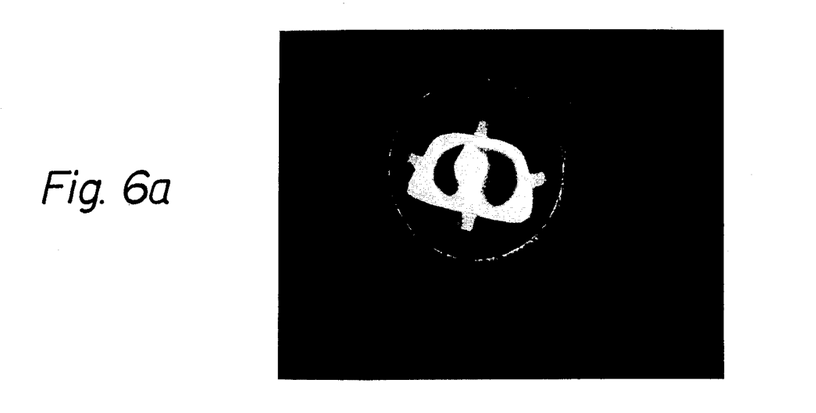
FIG. 6a is a reconstruction of body cross-section phantom from data obtained with the phantom rotated in a fixed beam.

A full evaluation of the system's performance has not yet been carried out, as modifications to provide couch twist and to increase the field of view have only recently been completed. During the development stages a series of phantom scans were carried out to test the system and the image reconstruction programs. FIG. 6a shows a reconstruction of a tissue equivalent body phantom held by four supporting blocks in a rotating jig. The 256*256 pixel image is reconstructed from 90 fixed angle projections and has reconstructed pixels of 0.15*0.15 cm. The reconstruction program did not include the correction for detector movement.

Figure 6B:
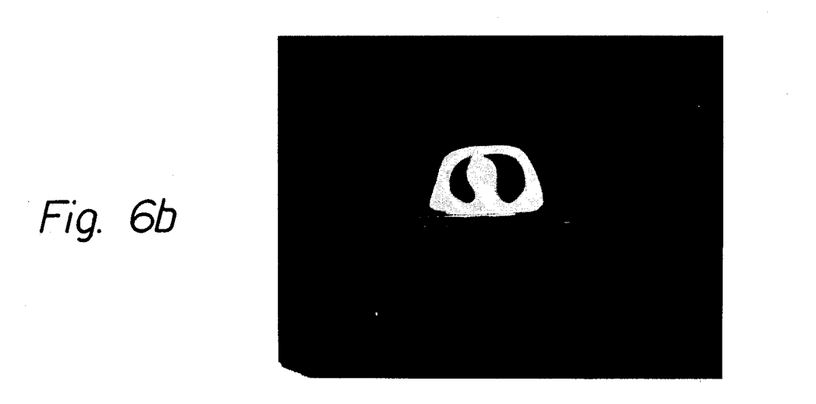
FIG. 6b is a reconstruction of body cross-section phantom from data obtained in continuous full rotation.
Figure 7A:
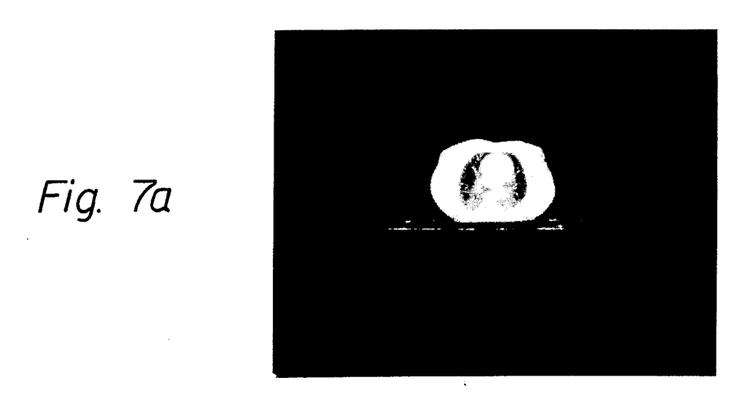
FIG. 7a shows a CT reconstruction of a slice through the breast of a female patient undergoing radiotherapy following removal of an adenosarcoma from the left breast.
Figure 7B:
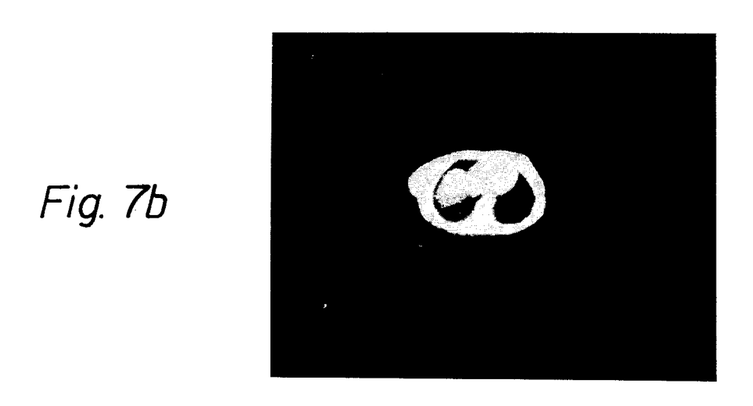
FIG. 7b shows a CT reconstruction of a slice through the breast of a female patient undergoing radiotherapy.

Using the scanner in continuous full rotational mode, a CT scan of the same body cross-section phantom was made (FIG. 6b). This shows that the spatial resolution is adequate for treatment planning. Other phantom experiments have been made with simple objects to confirm the geometrical fidelity of the reconstructed images. A series of scans have been performed on patients undergoing radiotherapy at the Royal Marsden Hospital, Sutton. FIG. 7a shows a reconstruction of a section through the breast of a female aged 42, undergoing radiotherapy following excision of an adenosarcoma from the left breast. The orientation is that used in conventional body CT. The image was reconstructed from 84 projections from a 10 min scan, reconstruction of a 256*256 image taking 22 min with no array processor, and displayed in the range 20-100% of the maximum level. The patient's outline, lung contours and bone structure are clearly evident. Other anatomical information is also evident although not required, including the descending aorta, pulmonary bronchii, heart and spinal canal. FIG. 7b shows a cross-section through a 48 year old patient undergoing post-operative radiotherapy to the left breast. The image was reconstructed from 72 projections acquired at the faster scan speed, taking half the scan time required for FIG. 7a, and shows little reduction in quality. The 10 min and 5 min scans required total surface doses of 0.2 and 0.1 Gy respectively to a thin section (approximately 1 cm) of the patient's thorax. The dose delivered prior to data acquisition is approximately 1% of the total dose.

This CT scanner based on a modified radiotherapy simulator has proved capable of obtaining satisfactory information for planning the treatment of organs or regions of the body rather than localized regions within organs and provides the facilities that are necessary for this purpose. Modifications that have recently been completed have increased the reconstructed field to 48 cm diameter (from 37 cm), whilst providing an aperture of 84 cm diameter. The scanner has been provided with couch twist about the centre of the CT slice, film simulation facilities and a permanent isocentric mounting. The combination of a large reconstructed field and a large aperture is a particular advantage of this sytem. The digital acquisition of data and processing of the data results in images which are free of the non-linearities which can result from the use of analog acquisition and reconstruction methods. The interfaces between lung and soft tissue are clearly delineated, as are the body outline and the position of bone structure. The contribution of the data to radiotherapy planning is currently being assessed. Current modifications to the equipment may be expected to further improve image quality.

As will be apparent from the preceding description, the illustrated embodiment of the invention provides a high count-rate position-sensitive detector of novel design permiting CT information to be obtained using a modified radio therapy simulator. In its illustrated form, the scanner is designed principally for planning the dosimetry of breast cancer radiotherapy. During the collection of transmission projection data, suitable for the digital reconstruction of patient cross-sections, the simulator gantry rotates continuously through about 360 degrees. A film cassette holder can be positioned above the detector to provide conventional simulator check films.

Cross-sections through patients receiving post-operative radiotherapy for breast cancer have been reconstructed from projections acquired with the patient lying in the treatment position. These scans are an average over the breathing cycle. The outlines of internal anatomy and the patient external contour have been used to produce treatment plans which include tissue inhomogeneity corrections. The data produced by this wide aperture CT scanner are suitable for planning those conditions where radiotherapy is delivered to an organ such as the breast, or the whole body, rather than to a localised lesion.

The disclosure of the following prior documents is incorporated herein by way of reference:

Herman, G. T. 1982 Journal of Medical Systems 6 555-568

Leach, M. O., Flatman, W., Webb, S., Flower, M. A. and Ott, R. J. 1983 in Proceedings of the 8th Information Processing in Medical Imaging Conference Brussels (In press).

Suit, M. D. 1982 Cancer 50 1227–1234

Webb, S. and Leach, M. O. 1980 in Computerised Axial Tomography in Oncology ed. J. Husband ad P. A. Hobday (Edinburgh:Churchill-Livingstone) pp 154–69 Webb, S. 1982 Phys. Med. Biol. 27 419–24.

We claim:

1. A CT scanner comprising: an X-ray source arranged to provide a fan-shaped beam of X-rays; an X-ray detector for producing an electrical output representative of scanning of an X-ray intensity across the fan-shaped beam; and means mounting the X-ray source and X-ray detector in a predetermined relationship with a space therebetween to accommodate a patient wherein the X-ray detector comprises a body of X-ray sensitive material extending across the fan and disposed inside a cylindrical X-ray opaque shutter comprising two cylindrical masking layers, each of the two cylindrical masking layers including means defining a helical slot therein extending lengthwise of and circumferentially of the cylindrical layer to form an X-ray transmissive aperture extending lengthwise of and circumferentially of the cylindrical layer in which it is defined, the two cylindrical masking layers being arranged one inside the other to form an inner and an outer mask with one of the apertures in part overlying the other so defining an exposed area of the X-ray sensitive material, and drive means operatively connected by coupling means to the cylindrical masking layers, the coupling means being adapted to drive said cylindrical masking layers in synchronous relative rotation during scanning of the fan-shaped beam so that the masks move relative to one another so as to move the exposed area lengthwise of the scintillator and across the fan.

2. A CT scanner according to claim 1, wherein the mounting means comprise a rotatable gantry so that the X-ray source and X-ray detector are rotatable around the patient.

3. A CT scanner according to claim 1, wherein the fan-shaped beam lies in a plane and has a central axis, and the X-ray detector is positioned to scan in the plane of the fan-shaped beam, along a line in a plane perpendicular to the central axis of the fan-shaped beam.

4. A CT scanner according to claim 3, wherein the line is straight.

5. A CT scanner according to claim 1, wherein the detector is a photon-counting detector.

6. A CT scanner according to claim 1, wherein the X-ray sensitive material is an elongate scintillator having two ends, and a photoelectric converting arrangement for producing electrical signals in response to photons produced by exposure of an area of the scintillator is provided at at least one end of the scintillator.

7. A X-ray detector comprising: an elongate scintillator disposed inside a cylindrical X-ray opaque shutter and having an area which in use is exposed to X-rays; a photoelectric converting arrangement for producing electrical signals in response to photons produced by exposure of said area of the scintillator; and means for moving the exposed area lengthwise of the scintillator, the means for moving the exposed area comprising two cylindrical masking layers forming said cylindrical X-ray opaque shutter, each of the two cylindrical masking layers including means defining a helical slot therein extending lengthwise of and circumferentially of the cylindrical layer to form an X-ray transmissive aperture extending lengthwise of and circumferentially of the cylindrical layer in which it is defined, the two cylindrical masking layers being arranged one inside the other to form an inner and an outer mask with one of the apertures in part overlying the other, so defining the exposed area of the scintillator, and drive means operatively connected by coupling means to the cylindrical masking layers, the coupling means being adapted to drive said cylindrical masking layers in synchronous relative rotation so that the masks move relative to one another so as to move the exposed area lengthwise of the scintillator, the photo-electric converting arrangement being responsive to scintillations caused in the scintillator by the photons to produce an electrical signal representative of a scan of X-ray intensity across the scintillator.

8. An X-ray detector according to claim 7 wherein the masking layers are cylindrical and concentric with one another and with the scintillator, at least one of the apertures conforming to a helix.

9. An X-ray detector according to claim 8 wherein both apertures conform to a helix.

10. An X-ray detector according to claim 7 wherein the photo-electric converting arrangement comprises photo detectors at each end of the scintillator and means are provided to sum the outputs of the photo detector and to count the photons detected.

* * * * *

UNITED STATES PATENT AND TRADEMARK OFFICE
CERTIFICATE OF CORRECTION

PATENT NO. : 4,769,829
DATED : September 6, 1988
INVENTOR(S) : Steve Webb et al

It is certified that error appears in the above-identified patent and that said Letters Patent is hereby corrected as shown below:

At Column 4, line 7, change "1.8" to --1.8 kV--.

Signed and Sealed this

Twelfth Day of September, 1989

Attest:

DONALD J. QUIGG

*Attesting Officer*      *Commissioner of Patents and Trademarks*